United States Patent
Kodama

(10) Patent No.: US 11,914,138 B2
(45) Date of Patent: Feb. 27, 2024

(54) DISTAL END FRAME OF ENDOSCOPE, DISTAL END UNIT, AND ENDOSCOPE

(71) Applicant: OLYMPUS CORPORATION, Tokyo (JP)

(72) Inventor: Daichi Kodama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 441 days.

(21) Appl. No.: 17/405,574

(22) Filed: Aug. 18, 2021

(65) Prior Publication Data

US 2021/0382293 A1 Dec. 9, 2021

Related U.S. Application Data

(63) Continuation of application No. PCT/JP2019/013830, filed on Mar. 28, 2019.

(51) Int. Cl.
*A61B 1/045* (2006.01)
*G02B 23/24* (2006.01)
(Continued)

(52) U.S. Cl.
CPC ..... *G02B 23/2484* (2013.01); *G02B 23/2423* (2013.01); *G02B 23/2461* (2013.01);
(Continued)

(58) Field of Classification Search
CPC ... A61B 1/0014; A61B 1/00133; A61B 1/045; A61B 1/0676; H04N 5/2252;
(Continued)

(56) References Cited

U.S. PATENT DOCUMENTS

| 5,857,963 A | 1/1999 | Pelchy et al. |
| 2009/0259101 A1* | 10/2009 | Unsai ............ A61B 1/05 600/110 |

(Continued)

FOREIGN PATENT DOCUMENTS

| CN | 106061350 A | 10/2016 |
| JP | 2000-060793 A | 2/2000 |

(Continued)

OTHER PUBLICATIONS

International Search Report dated Jun. 25, 2019 received in PCT/JP2019/013830.

*Primary Examiner* — Patrick E Demosky
(74) *Attorney, Agent, or Firm* — Scully, Scott, Murphy & Presser, P.C.

(57) ABSTRACT

A distal end frame includes: a distal end frame body including a resin molded product; an image pickup unit housing chamber formed of a bottomed hole with an opening which is formed on a distal end surface of the distal end frame body; a through hole penetrating from a bottom face of the image pickup unit housing chamber to a proximal end side of the distal end frame body; a mounting face formed on the bottom face of the image pickup unit housing chamber; an inclined face that is formed in a region containing a part of an inner wall face of the through hole to be adjacent to the mounting face, and is visible through the opening; and a wiring pattern that is formed of the metal pattern constituting the molded interconnect device, and is continuously formed in a region containing the mounting face and the inclined face.

8 Claims, 12 Drawing Sheets

(51) Int. Cl.
*H04N 23/51* (2023.01)
*H04N 23/57* (2023.01)
*H04N 23/50* (2023.01)

(52) U.S. Cl.
CPC ............. *H04N 23/51* (2023.01); *H04N 23/57* (2023.01); *H04N 23/555* (2023.01)

(58) Field of Classification Search
CPC .... H04N 5/2253; H04N 5/2258; H04N 23/51; H04N 23/57; H04N 23/555; G02B 23/2484; G02B 23/2423; G02B 23/2461
See application file for complete search history.

(56) References Cited

U.S. PATENT DOCUMENTS

| | | | |
|---|---|---|---|
| 2015/0216399 A1 | | 8/2015 | Stuehle et al. |
| 2016/0037029 A1* | | 2/2016 | Igarashi ................. H04N 23/51 |
| | | | 348/65 |

FOREIGN PATENT DOCUMENTS

| | | |
|---|---|---|
| JP | 2000-092477 A | 3/2000 |
| JP | 2015-528336 A | 9/2015 |
| JP | 2017-023234 A | 2/2017 |
| JP | 2017-505154 A | 2/2017 |
| JP | 2017-113417 A | 6/2017 |
| WO | 2014/037067 A1 | 3/2014 |
| WO | 2015/082328 A1 | 6/2015 |
| WO | 2016/092986 A1 | 6/2016 |

\* cited by examiner

DISTAL END FRAME OF ENDOSCOPE, DISTAL END UNIT, AND ENDOSCOPE

CROSS REFERENCE TO RELATED APPLICATION

This application is a continuation application of PCT/JP2019/013830 filed on Mar. 28, 2019, the entire contents of which are incorporated herein by this reference.

BACKGROUND OF THE INVENTION

1. Field of the Invention

The present invention relates to: a distal end frame of an endoscope provided with an image pickup unit inside the distal end frame; a distal end unit; and an endoscope.

2. Description of the Related Art

Conventionally, in order to observe a site where direct visual observation is difficult, such as an internal part of a living body or a structural object, an endoscope which is configured to be introduced from an outside of the living body or the structural object toward inside and has such a structure as to be capable of forming an optical image or picking up the optical image is widely used in the medical field or industrial field.

In such an endoscope, a distal end portion provided at a distal end of an insertion portion is mainly composed of a distal end unit in which various functional components are provided on a hard distal end frame. As a distal end frame of such a distal end unit, a distal end frame using a technology of molded interconnect devices (MIDs) has been proposed in recent years. For example, in International Publication WO 2015/082328, an endoscope head (distal end unit of endoscope) is disclosed, which includes: a head body (distal end frame) that is formed of an MID element in which a plurality of electroconductive paths are formed; and various electronic components such as a camera module (image pickup unit), to which an electric power is supplied through the electroconductive paths.

Here, in the MID technology, a metal pattern can be formed only on a resin surface which can be irradiated with a laser beam or the like. Accordingly, the technology disclosed in the above described International Publication WO 2015/082328 adopts a configuration in which an opening is provided on one side of a camera housing space (image pickup unit housing chamber), and electroconductive paths (wiring pattern) which are electrically connected to the camera module are formed on an outer peripheral surface of the distal end frame continuous to the opening.

SUMMARY OF THE INVENTION

A distal end frame of an endoscope according to one aspect of the present invention includes: a distal end frame body that includes a resin molded product which constitutes a molded interconnect device having a metal pattern formed on a surface of the resin molded product; a housing chamber that is formed of a bottomed hole with an opening which is formed on an outer surface of the distal end frame body and is configured to open up an internal space, and that is configured to house an electronic component in an inside of the distal end frame body; a through hole that penetrates from a part of a bottom face of the housing chamber to a proximal end side of the distal end frame body; a first face that is formed on the bottom face of the housing chamber and on which the electronic component is mounted; a first connection land that is formed of the metal pattern constituting the molded interconnect device and is formed on the first face to electrically connect the electronic component; a second face that is formed in a region containing a part of an inner wall face of the through hole to be adjacent to the first face, and is visible through the opening; and a wiring pattern that is formed of the metal pattern constituting the molded interconnect device, is electrically connected to the first connection land, and is continuously formed in a region containing the first face and the second face.

In addition, a distal end unit of an endoscope according to one aspect of the present invention includes: a distal end frame; and an electronic component that is housed in a housing chamber of the distal end frame and is electrically connected to a first connection land. The distal end frame includes: a distal end frame body that includes a resin molded product which constitutes a molded interconnect device having a metal pattern formed on a surface of the resin molded product; a housing chamber that is formed of a bottomed hole with an opening which is formed on an outer surface of the distal end frame body and is configured to open up an internal space, and that is configured to house the electronic component in an inside of the distal end frame body; a through hole that penetrates from a part of a bottom face of the housing chamber to a proximal end side of the distal end frame body; a first face that is formed on the bottom face of the housing chamber and on which the electronic component is mounted; a first connection land that is formed of the metal pattern constituting the molded interconnect device and is formed on the first face to electrically connect the electronic component; a second face that is formed in a region containing a part of an inner wall face of the through hole to be adjacent to the first face, and is visible through the opening; and a wiring pattern that is formed of the metal pattern constituting the molded interconnect device, is electrically connected to the first connection land, and is also continuously formed in a region containing the first face and the second face.

In addition, an endoscope according to one aspect of the present invention includes in a distal end portion of an insertion portion: a distal end frame; and an electronic component that is housed in a housing chamber of the distal end frame and is electrically connected to a first connection land. The distal end frame includes: a distal end frame body that includes a resin molded product which constitutes a molded interconnect device having a metal pattern formed on a surface of the resin molded product; a housing chamber that is formed of a bottomed hole with an opening which is formed on an outer surface of the distal end frame body and is configured to open up an internal space, and that is configured to house the electronic component in an inside of the distal end frame body; a through hole that penetrates from a part of a bottom face of the housing chamber to a proximal end side of the distal end frame body; a first face that is formed on the bottom face of the housing chamber and on which the electronic component is mounted; a first connection land that is formed of the metal pattern constituting the molded interconnect device and is formed on the first face to electrically connect the electronic component; a second face that is formed in a region containing a part of an inner wall face of the through hole to be adjacent to the first face, and is visible through the opening; and a wiring pattern that is formed of the metal pattern constituting the molded interconnect device, is electrically connected to the first connection land, and is also continuously formed in a region containing the first face and the second face.

DETAILED DESCRIPTION OF THE PREFERRED EMBODIMENTS

Figure 1:
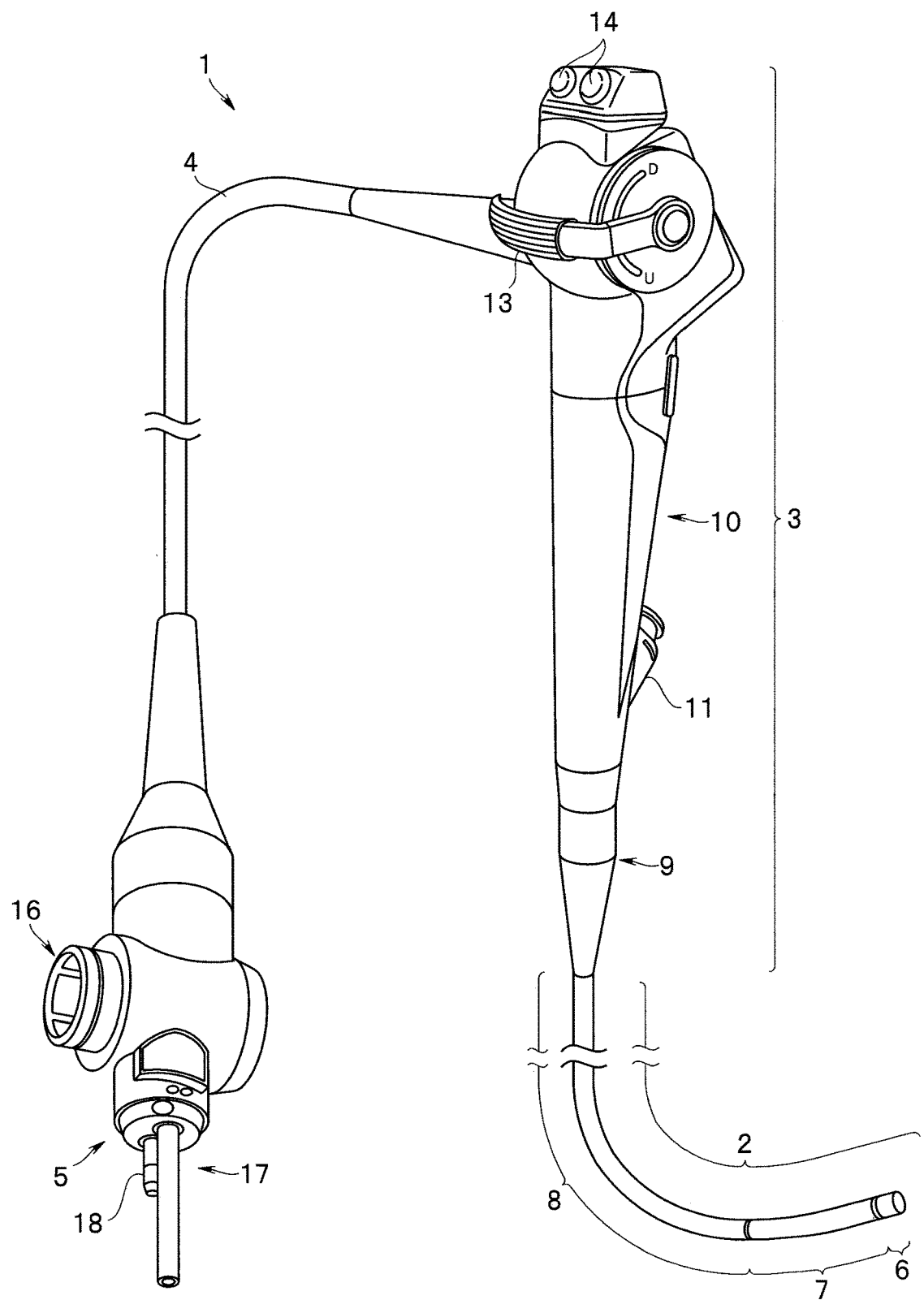
FIG. 1 is an external perspective view of an endoscope according to a first embodiment of the present invention.

Embodiments of the present invention will be described below with reference to drawings. FIG. 1 to FIG. 6 relate to a first embodiment of the present invention, and FIG. 1 is an external perspective view of an endoscope.

The endoscope 1 shown in FIG. 1 includes: an insertion portion 2 with an elongated shape (long shape), which is inserted into a body cavity of a subject; an operation section 3 that is provided continuously to a proximal end of the insertion portion 2; a universal cable 4 that extends from the proximal end of the operation section 3; and an endoscope connector 5 that is arranged at an extending end of the universal cable 4.

The insertion portion 2 is a tubular member having flexibility, in which a distal end portion 6, a bending portion 7, and a flexible tube portion 8 are continuously provided in this order from the distal end side.

Figure 2:
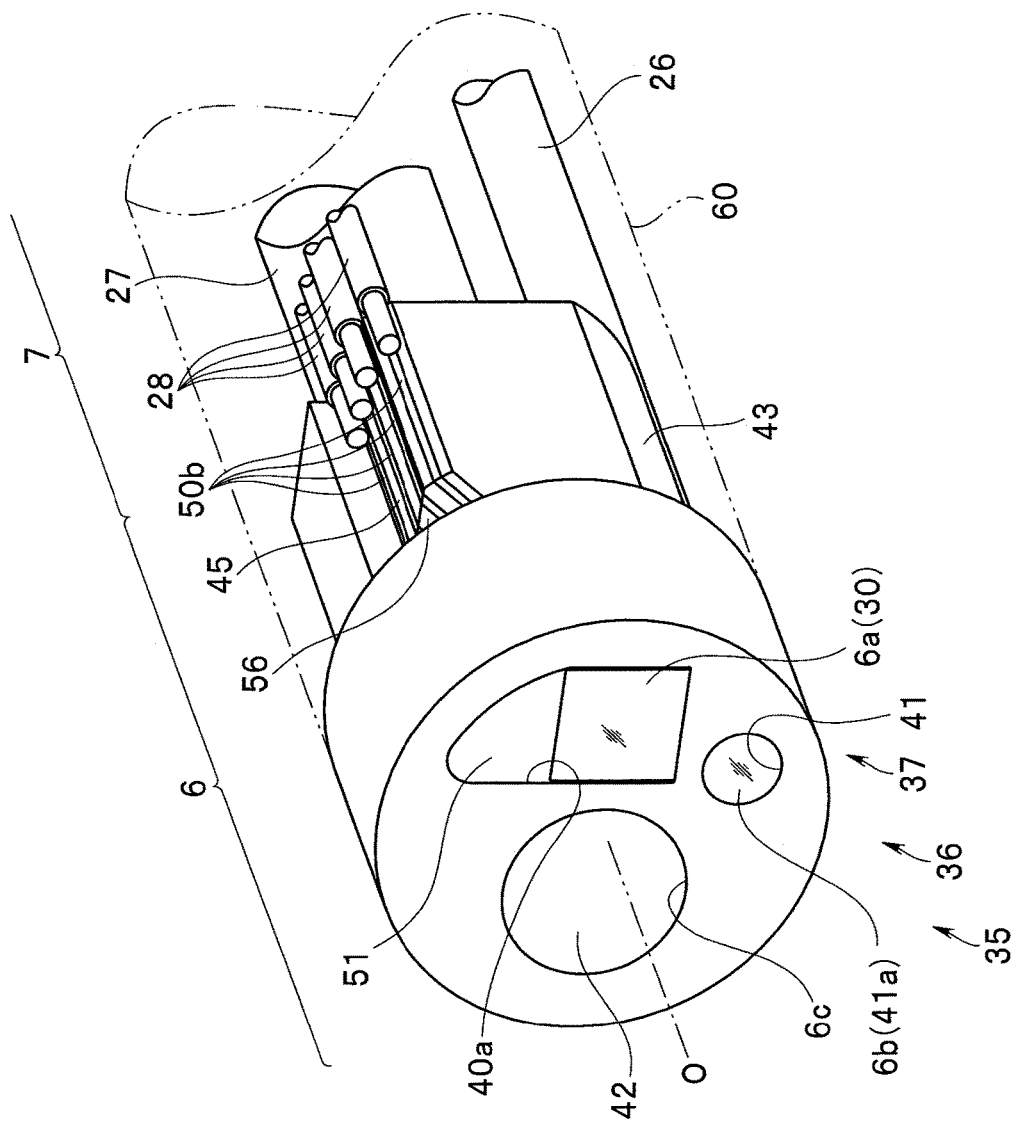
FIG. 2 is an external perspective view of a distal end unit according to the first embodiment of the present invention.

As shown in FIG. 2, an observation window 6a through which a subject is observed, an illumination window 6b through which the subject is irradiated with illumination light, and a channel opening 6c with which a distal end side of a treatment instrument channel 27 communicates are arranged on a distal end surface of the distal end portion 6.

In addition, an image pickup unit 25 as an electronic device configured to pick up an optical image of the subject is arranged inside the distal end portion 6, and also a distal end side of a light guide 26 configured to guide illumination light to be applied to the subject, to the distal end portion 6 through the illumination window 6b, and the like are arranged.

The bending portion 7 is a mechanical site that is configured to be actively bent, for example, in two upward and downward bending directions (up-down). Note that in the present embodiment, up-and-down and left-and-right directions of the insertion portion 2 and the like are defined for convenience to correspond with up-and-down and left-and-right directions of an endoscope image to be picked up by the image pickup unit 25.

The flexible tube portion 8 is a tubular member that is configured to have flexibility to become passively flexible. Various cables 28 that are electrically connected to the image pickup unit 25 and the like, the light guide 26, the treatment instrument channel 27 and the like are inserted in an inside of the flexible tube portion 8.

The operation section 3 includes: a bend preventing portion 9 that is connected to the flexible tube portion 8 in a state of covering the proximal end of the flexible tube portion 8; and a grip portion 10 that is provided continuously to a proximal end side of the bend preventing portion 9 and can be gripped by the hand of a user.

A treatment instrument insertion portion 11 that communicates with a proximal end side of the treatment instrument channel 27 is provided on a distal end side of the grip portion 10. In addition, an operation lever 13 for performing a bending operation of the bending portion 7, and an operation switch 14 to which various functions of the endoscope 1 are assigned are provided on the proximal end side of the grip portion 10.

The universal cable 4 is a composite cable that allows insertion of, for example, the various cables 28 extending from the distal end portion 6 of the insertion portion 2, the light guide 26 and the like, inside, and that also allows insertion of an air/water feeding tube (not illustrated) a distal end side of which is connected to the treatment instrument channel 27, inside.

The endoscope connector 5 includes: an electrical connector portion 16 configured to connect the various cables 28 to a video processor (not illustrated) which is an external device; a light source connector portion 17 configured to connect the light guide 26 to a light source device (not illustrated) which is an external device: and an air/water feeding plug 18 configured to connect an air/water feeding tube to an air/water feeding device (not illustrated) which is as an external device.

Next, a configuration of the distal end portion 6 will be more specifically described with reference to FIG. 2 to FIG. 6.

The distal end portion 6 of the present embodiment is mainly composed of a distal end unit 35 that has various functional components such as the image pickup unit 25 provided in a distal end frame 36 having a hard and approximately columnar shape formed of a molded interconnect device (MID).

Figure 3:
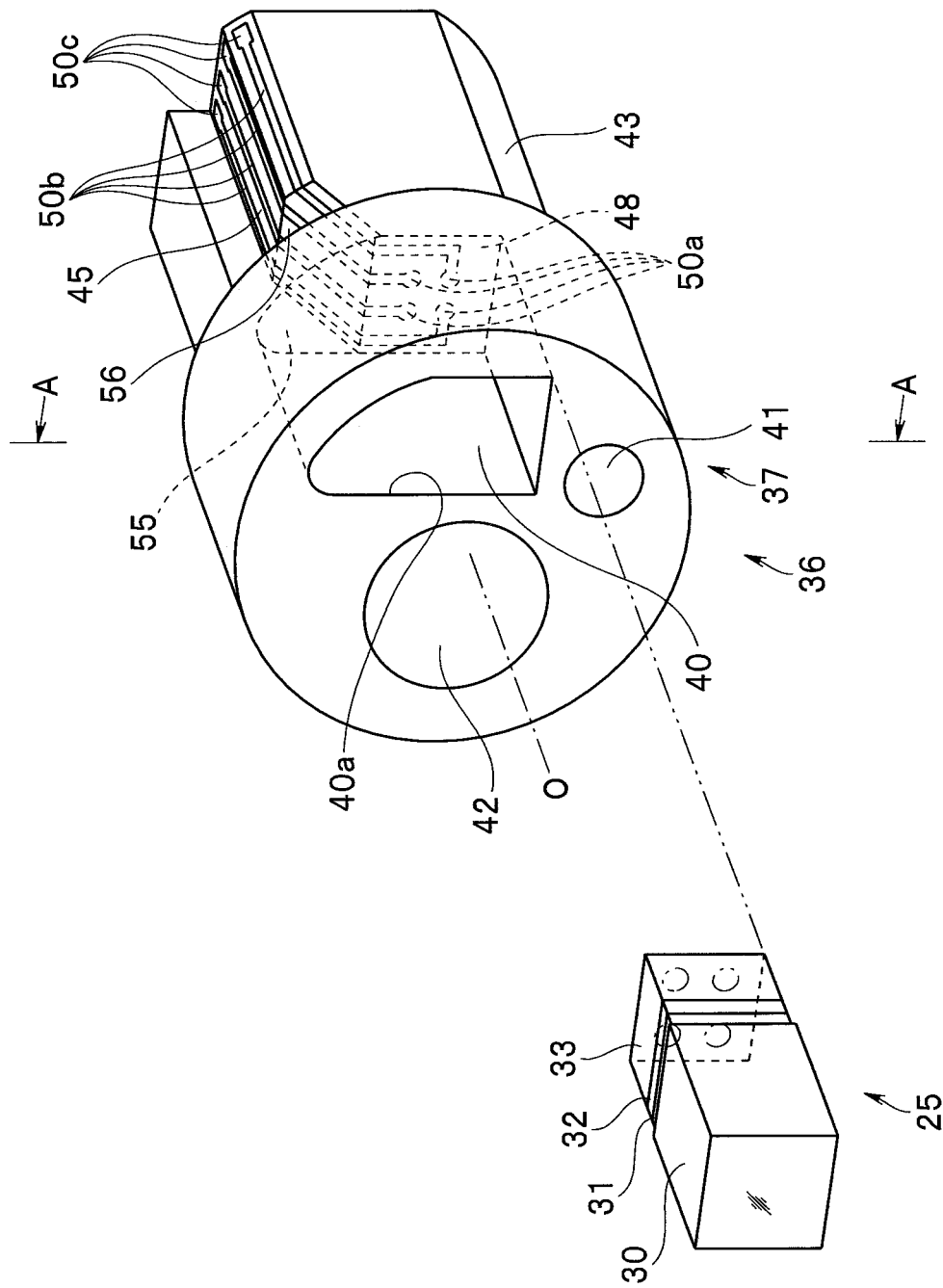
FIG. 3 is an exploded perspective view showing a distal end frame and an image pickup unit according to the first embodiment of the present invention.
Figure 4:
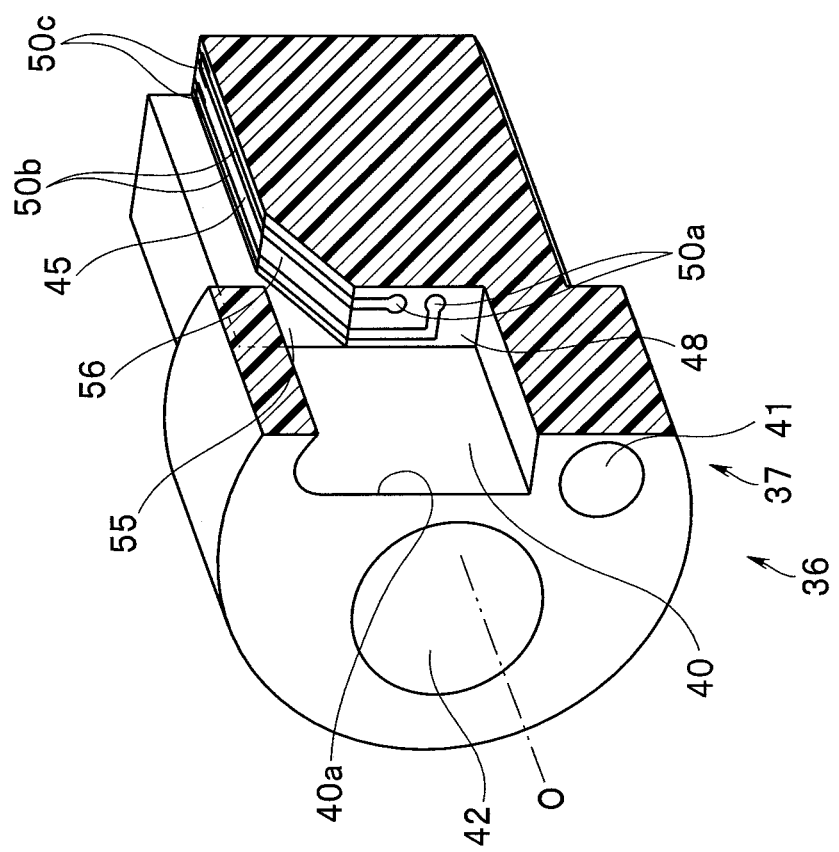
FIG. 4 is a sectional perspective view of the distal end frame along a line A-A in FIG. 3, according to the first embodiment of the present invention.

Here, in the present embodiment, for example, as shown in FIG. 3, the image pickup unit 25 provided in the distal end frame 36 as one of the functional components is composed of a CSP (chip size package) in which a lens unit 30 for image pickup composed of a lens laminate produced with the use of a wafer-level optics technique; a cover glass 31, and an image pickup device 33 which is stuck on the cover glass 31 via an adhesive layer 32 are integrally packaged. In such an image pickup unit 25, the lens unit 30 for image pickup is manufactured, for example, by preparing a plurality of lens wafers in which lenses are formed on a base material such as a glass substrate, and stacking and dicing the lens wafers. Because of this, the lens unit 30 for image pickup of the present embodiment is a lens unit that has a rectangular shape in plan view and does not have a lens frame. In addition, the image pickup device 33 is also formed into a rectangular shape in plan view by dicing or the like, and the image pickup unit 25 of the present embodiment has an approximately rectangular parallelepiped shape as a whole.

The distal end frame 36 includes, for example, a distal end frame body 37 that is formed by injection molding with the use of a resinous material and has an approximately pillar shape (in the present embodiment, more specifically, approximately columnar shape). In the distal end frame body 37, a part of the distal end surface and the outer peripheral surface is exposed on the surface of the distal end portion 6, and forms an external shape of the distal end portion 6 in an intact state. For the reason, a material that not only is compatible with the MID technology but also has biocompatibility has been selected for the resinous material that constitutes the distal end frame body 37. Here, in the present embodiment, the distal end frame body 37 refers to, for example, a resin portion formed by injection molding; and various wiring patterns and the like (which will be described later) are formed on a surface of the distal end frame body 37 by a metal pattern with the use of the MID technology, and thereby, the distal end frame 36 is structured.

In the distal end frame body 37, there are formed an image pickup unit housing chamber 40 that is a housing chamber configured to house the image pickup unit 25 which is an optical functional component, a light source housing chamber 41 that is a housing chamber configured to house a distal end side of the light guide as a light source which is an optical functional component, and a channel holding chamber 42 configured to hold a distal end side of the treatment instrument channel 27.

In addition, a step is formed on an outer periphery of the distal end frame body 37, in order to cause an outer diameter of the proximal end side to be smaller than an outer diameter of the distal end side, and a region on the proximal end side, which is caused to be smaller by the step, is set as a fitting portion 43 configured to be connected by fitting to a cylindrical cover member 60 which constitutes the bending portion 7.

Furthermore, a plurality of flat faces that extend in an insertion axis O direction are formed in the fitting portion 43, and one of these flat faces is set as a cable connection face 45 as a third surface configured to connect various cables. The cable connection face 45 in the present embodiment is also extended to a part of an arcuate surface that constitutes the fitting portion 43, to secure a sufficient area.

The image pickup unit housing chamber 40 is composed of a bottomed hole the depth direction of which is, for example, set in the insertion axis O direction. In such a way, the image pickup unit housing chamber 40 of the present embodiment is formed in the insertion axis O direction, and thereby, the bottom face is orthogonal to the insertion axis O, and an opening 40a that opens up the internal space is formed on the distal end surface which is one of the outer surfaces of the distal end frame body 37.

A part of a region on the bottom face of the image pickup unit housing chamber 40 is formed as a mounting face 48 which is a first face on which the image pickup unit 25 is mounted.

Figure 6:
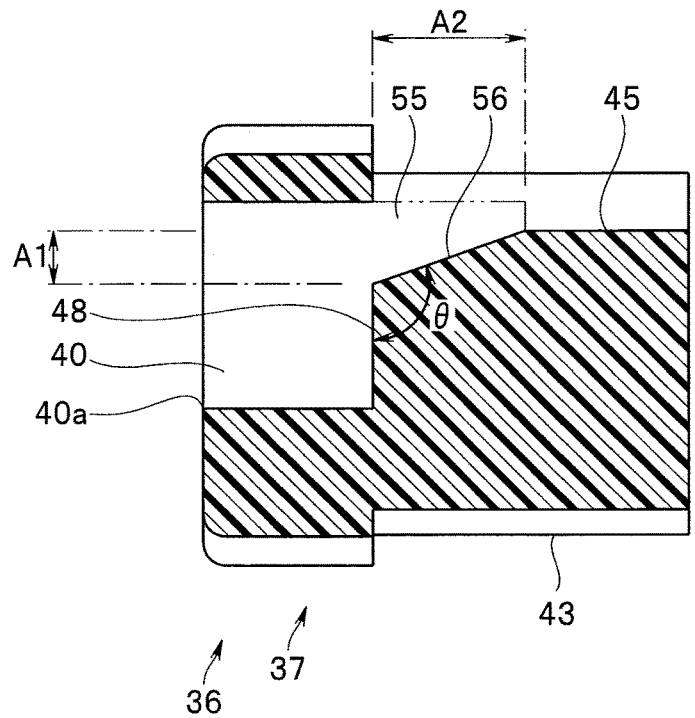
FIG. 6 is a cross-sectional view of the distal end frame along the line A-A in FIG. 3, according to the first embodiment of the present invention.

Note that in the present embodiment, a position of the mounting face 48 in the insertion axis O direction is set to be a same position as the step configured to form the fitting portion 43 on the outer periphery of the distal end frame body 37, as shown in FIG. 6, for example.

A plurality of (for example, four) first connection lands 50a are provided as a metal pattern, on the mounting face 48. The image pickup device 33 of the image pickup unit 25 is electrically connected to each of the first connection lands 50a by a material having electroconductivity. In such a way, the image pickup device 33 is connected to each of the first connection lands 50a, and thereby the image pickup unit 25 is held in the image pickup unit housing chamber 40, in a state in which an optical axis direction is positioned to match the insertion axis O direction.

Note that as the material having the electroconductivity for electrically connecting the image pickup device 33 to each of the first connection lands 50a, solder, an electroconductive adhesive or the like can be suitably used.

Furthermore, a plurality of (for example, four) wiring patterns 50b as metal patterns are provided on the mounting face 48, and one ends of the wiring patterns 50b are electrically connected to the respective first connection lands 50a.

In addition, in the bottom face of the image pickup unit housing chamber 40, a through hole 55 that extends in the depth direction (that is, insertion axis O direction) of the image pickup unit housing chamber 40 is provided in a region adjacent to the mounting face 48. In addition, due to the through hole 55, the internal space of the image pickup unit housing chamber 40 is allowed to communicate with a region in a proximal end side of the distal end frame body 37, in which the cable connection face 45 is formed.

Here, when the through hole 55 adjacent to the mounting face 48 is formed as above, the image pickup unit housing chamber 40 needs to be expanded by the corresponding space, but in the present embodiment, an expansion region for forming the through hole 55 is set in a direction orthogonal to a straight line connecting the observation window 6a and the channel opening 6c, and thereby the enlargement of the diameter of the distal end frame body 37 is suppressed. In other words, a space in such a direction becomes basically a dead space in many cases, and by effectively utilizing such a dead space, it becomes possible to secure a space for providing the through hole 55 without increasing the diameter of the distal end frame body 37.

In an inner wall face constituting the through hole 55, an inclined face 56 as a second face is formed in a part of a region which is provided continuously to the mounting face 48 and the cable connection face 45. The inclined face 56 is set at such an angle that an angle θ formed by the mounting face 48 is, for example, larger than 90 degrees and smaller than 180 degrees, as shown in FIG. 6. In other words, the inclined face 56 is inclined at a predetermined angle with respect to the insertion axis O direction, for example, to be displaced in the outer peripheral direction as the inclined face 56 heads from the distal end side to the proximal end side of the distal end frame body 37. In other words, the inclined face 56 is inclined with respect to the insertion axis O direction so that the opening area (opening area orthogonal to the insertion axis O direction) of the through hole 55 is gradually reduced from the distal end side to the proximal end side.

Figure 5:
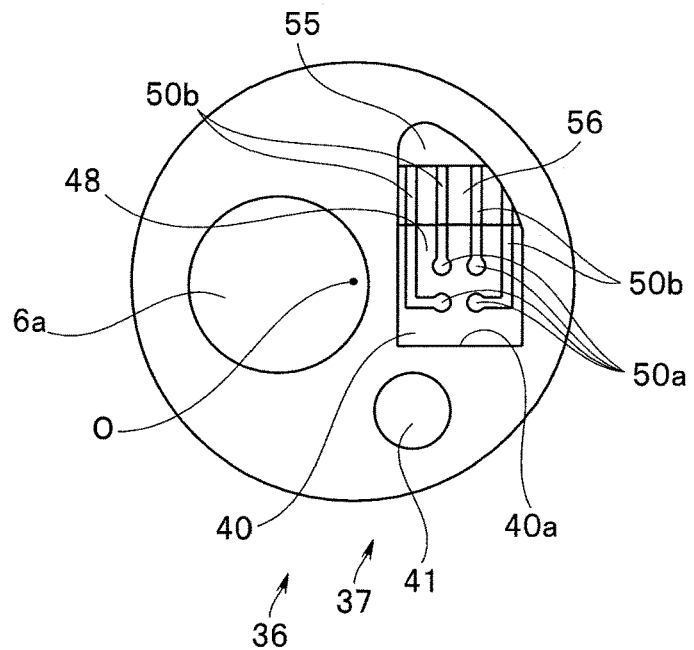
FIG. 5 is an end elevational view of the distal end frame according to the first embodiment of the present invention.

Thereby, for example, when the inside of the image pickup unit housing chamber 40 is viewed squarely from the opening 40a side as shown in FIGS. 5 and 6, the inclined face 56 and the mounting face 48 can be seen at the same time. In other words, the inclined face 56 of the present embodiment has a first region A1 that is visible in the insertion axis O direction through the opening 40a.

Furthermore, the fitting portion 43 is formed into a partially cut-out shape, and thereby in the inner wall face constituting the through hole 55, a part of a region is removed which includes a region facing the inclined face 56. Thereby, the inclined face 56 is exposed to a side of the fitting portion 43 (distal end frame body 37). By thus being exposed, the inclined face 56 and the cable connection face 45 can be seen at the same time. In other words, the inclined face 56 of the present embodiment has a second region A2 that is visible in a direction which intersects the insertion axis O direction (for example, orthogonal direction).

Here, the first region A1 and the second region A2 in the inclined face 56 are set so that the region A1 and the region A2 overlap at least partially, and in the present embodiment, as is clear from FIG. 6, the first region A1 and the second region A2 overlap completely.

Each of the wiring patterns 50b provided on the mounting face 48 is extended on the inclined face 56, and each of the wiring patterns 50b is further extended on the cable connection face 45.

In addition, a plurality of (for example, four) second connection lands 50c as metal patterns are provided on the cable connection face 45, and the other end of each of the wiring patterns 50b is electrically connected to each of the second connection lands 50c, respectively. Each of the second connection lands 50c is electrically connected to a signal cable 28 which is inserted into the insertion portion 2, by a material having electroconductivity.

Here, each of the first connection lands 50a, each of the wiring patterns 50b and each of the second connection lands 50c are formed by the MID technology; and for example, are formed, after a resin surface which forms the distal end frame body 37 is activated by laser irradiation or the like, by metal plating being performed onto the resin surface, which has been activated.

In this case, when each of the wiring patterns 50b is formed, the mounting face 48 and the first region A1 of the inclined face 56, which can be seen at the same time in the insertion axis O direction through the opening 40a, are continuously irradiated with a laser beam; and the second region A2 of the inclined face 56 and the cable connection face 45, which can be seen at the same time in the direction orthogonal to the insertion axis O, are continuously irradiated with a laser beam. Because the first region A1 and the second region A2 overlap, consequently, the mounting face 48, the inclined face 56, and the cable connection face 45 can be continuously irradiated with a laser beam.

After the image pickup unit 25 has been connected to each of the first connection lands 50a, the inside of the image pickup unit housing chamber 40 is sealed with a filler 51 (see FIG. 2). The outer periphery of the image pickup unit 25 is covered with the filler 51, and thereby, the outer periphery of the image pickup unit 25 is liquid-tightly sealed. Furthermore, the filler 51 is integrally filled in the through hole 55 as well. Each of the first connection lands 50a and each of the wiring patterns 50b are insulated by the filler 51, in the region from the mounting face 48 to the inclined face 56.

Such a filler 51 is filled, for example, by adding a fluid of the filler having a predetermined viscosity dropwise into the image pickup unit housing chamber 40 and the through hole 55, and curing the filler. In this case, it is important to cause the fluid of the filler, which has been added dropwise, to flow in efficiently due to a surface tension, without causing the fluid to stay in one place, but the widths of the image pickup unit housing chamber 40 and the through hole 55 are as small as 0.5 mm to 1 mm, and accordingly, the filling work can be performed efficiently, by causing the fluid of the filler to flow in from the proximal end side of the through hole 55 along the inclined face 56.

The light source housing chamber 41 is composed, for example, of a through hole extending in the insertion axis O direction of the insertion portion 2. The light source housing chamber 41 is a circular hole a cross-sectional shape of which in the direction orthogonal to the insertion axis O is an approximately circular shape.

The light guide 26 is inserted into the light source housing chamber 41. Furthermore, an optical member 41a formed of an illumination lens, a cover glass or the like is attached to the light source housing chamber 41 closer to the distal end side than the light guide 26, the optical member 41a closes the distal end side of the light source housing chamber 41, and thereby an illumination window 6b is formed on the distal end surface of the distal end frame 36.

The channel holding chamber 42 is composed of a through hole extending in the insertion axis O direction of the insertion portion 2. The channel holding chamber 42 is a circular hole a cross-sectional shape of which in the direction vertical to the insertion axis O is an approximately circular shape.

In the channel holding chamber 42, the treatment instrument channel 27 is fixed via an unillustrated pipe sleeve. In addition, the channel opening 6c is formed at the distal end side of the channel holding chamber 42.

At the proximal end side of the distal end unit 35 configured as above, a cylindrical cover member 60 which constitutes the bending portion 7 is connected to the fitting portion 43 by fitting. The cover member 60 is arranged to cover the through hole 55 filled with the filler 51, and the cable connection face 45, and is fixed to the fitting portion 43 via an adhesive agent or the like. The cover member 60 is fixed in the above, and thereby, the proximal end side of the distal end unit 35 is liquid-tightly sealed.

s that is formed of the bottomed hole with the opening 40a which is formed on the distal end surface of the distal end frame body 37 and is configured to open up the internal space, and that houses the image pickup unit 25 inside the distal end frame body 37; the through hole 55 that penetrates from the part of the bottom face of the image pickup unit housing chamber 40 to the proximal end side of the distal end frame body 37; the mounting face 48 that is formed on the bottom face of the image pickup unit housing chamber 40 and on which the image pickup unit 25 is mounted; the first connection lands 50a that are formed of the metal pattern constituting the molded interconnect device and is formed on the mounting face 48 to electrically connect the image pickup unit 25; the inclined face 56 that is formed in the region including the part of the inner wall face of the through hole 55 to be adjacent to the mounting face 48, and is inclined in the depth direction of the image pickup unit housing chamber 40 to be visible from the opening 40a; and the wiring patterns 50b that are formed of the metal pattern constituting the molded interconnect device, is electrically connected to the first connection lands 50a, and is continuously formed in the region containing the mounting face 48 and the inclined face 56. Thereby, the distal end unit of the endoscope can surely protect the image pickup unit 25 to be mounted, secure the insulation of the wiring patterns 50b, and at the same time, decrease the diameter of the distal end portion 6.

In other words, by providing the through hole 55 that communicates with the proximal end side of the distal end frame body 37 on the bottom face of the image pickup unit housing chamber 40, and forming the wiring patterns 50b in the region containing the through hole 55, the electrical connection from the mounting face 48 to the proximal end side of the distal end frame body 37 can be realized without providing the wiring patterns 50b on the outer surface of the distal end frame body 37. In addition, by filling the through hole 55 in which the wiring patterns 50b are formed with the filler 51 having insulating properties, the insulation of the wiring patterns 50b can be realized without providing a cap or the like for the distal end frame 36.

In this case, providing the inclined face 56 that is inclined in the depth direction of the image pickup unit housing chamber 40 in the through hole 55, and forming the wiring pattern 50 on the inclined face 56 for the inside of the through hole 55, the wiring patterns 50b with satisfactory continuity can be formed, even when the MID technology is used.

In other words, by forming the inclined face 56 on the part of the inner wall face of the through hole 55, and causing the mounting face 48 and the inclined face 56 to be visible at the same time in the insertion axis O direction through the opening 40a, the mounting face 48 and the inner wall face of the through hole 55 can be continuously irradiated with the laser beam configured to form the wiring patterns 50b.

In addition, by forming the fitting portion 43 of the distal end frame body 37 to have such a shape that the part of the region containing the region facing the inclined face 56 in the inner wall face constituting the through hole 55 is removed, and causing the inclined face 56 and the cable connection face 45 to be visible at the same time in the direction orthogonal to the insertion axis O direction, the inner wall face of the through hole 55 and the cable connection face 45 can be continuously irradiated with the laser beam configured to form the wiring patterns 50b.

Furthermore, by causing the region on the inclined face 56 visible in the insertion axis O direction (first region A1) and the region on the inclined face 56 visible in the direction orthogonal to the insertion axis O direction (second region A2) to overlap, consequently, the mounting face 48, the inclined face 56 and the cable connection face 45 can be continuously irradiated with the laser beam, and more suitable continuity of the wiring patterns 50b can be secured.

Furthermore, by providing the inclined face 56 between the mounting face 48 and the cable connection face 45, which is inclined at an obtuse angle greater than 90 degrees with respect to both of the faces, a bending angle of each of the wiring patterns 50b provided on the mounting face 48, inclined face 56 and the cable connection face 45 can be made obtuse, and suitable noise countermeasures for high-frequency signals can be realized.

In addition, by wiring the wiring patterns 50b through the through hole 55 as described above, it becomes unnecessary to cut out a part of the peripheral wall of the image pickup unit housing chamber 40, and it becomes possible to protect the entire periphery of the image pickup unit 25 by the peripheral wall of the image pickup unit housing chamber 40. Accordingly, also from the viewpoint of the protection of the image pickup unit 25, a cap or the like does not need to be provided on the distal end frame 36, and the diameter of the distal end portion 6 can be effectively decreased.

In addition, by providing the inclined face 56 in the through hole 55, when the distal end frame body 37 is molded, die-cutting in the through hole 55 can be easily realized.

Figure 7:
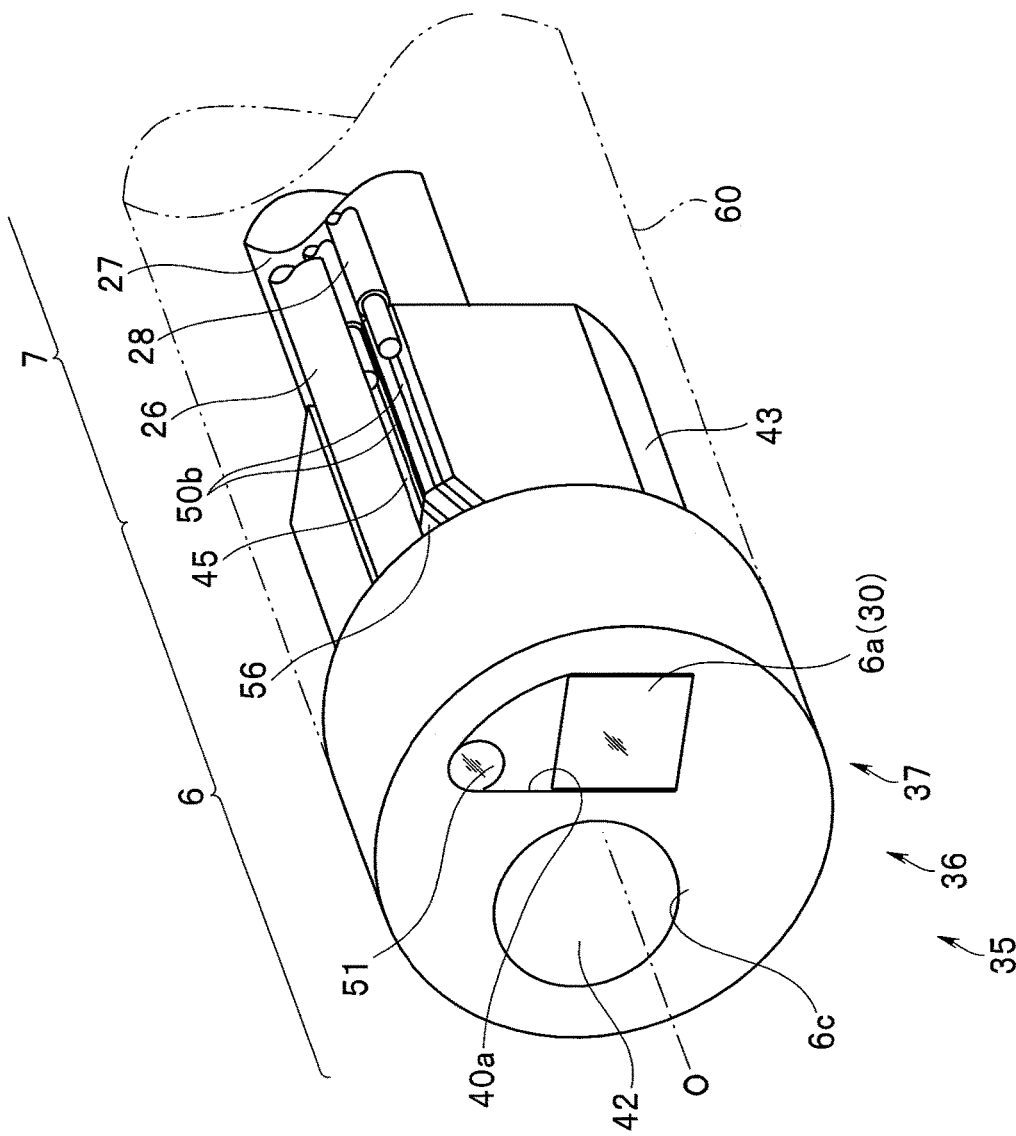
FIG. 7 is an external perspective view of a distal end unit according to a modification.

Here, for example, as shown in FIG. 7, it is also possible to use the image pickup unit housing chamber 40 as the light source housing chamber, and use the through hole 55 also as a through hole configured to allow insertion of the light guide 26.

In such a configuration, even when the through hole 55 is provided at a position adjacent to the mounting face 48, it is possible to prevent the region in which the through hole 55 is provided from becoming a dead space, to enhance the degree of freedom in designing of the distal end frame 36, and also to further decrease the diameter.

Figure 8:
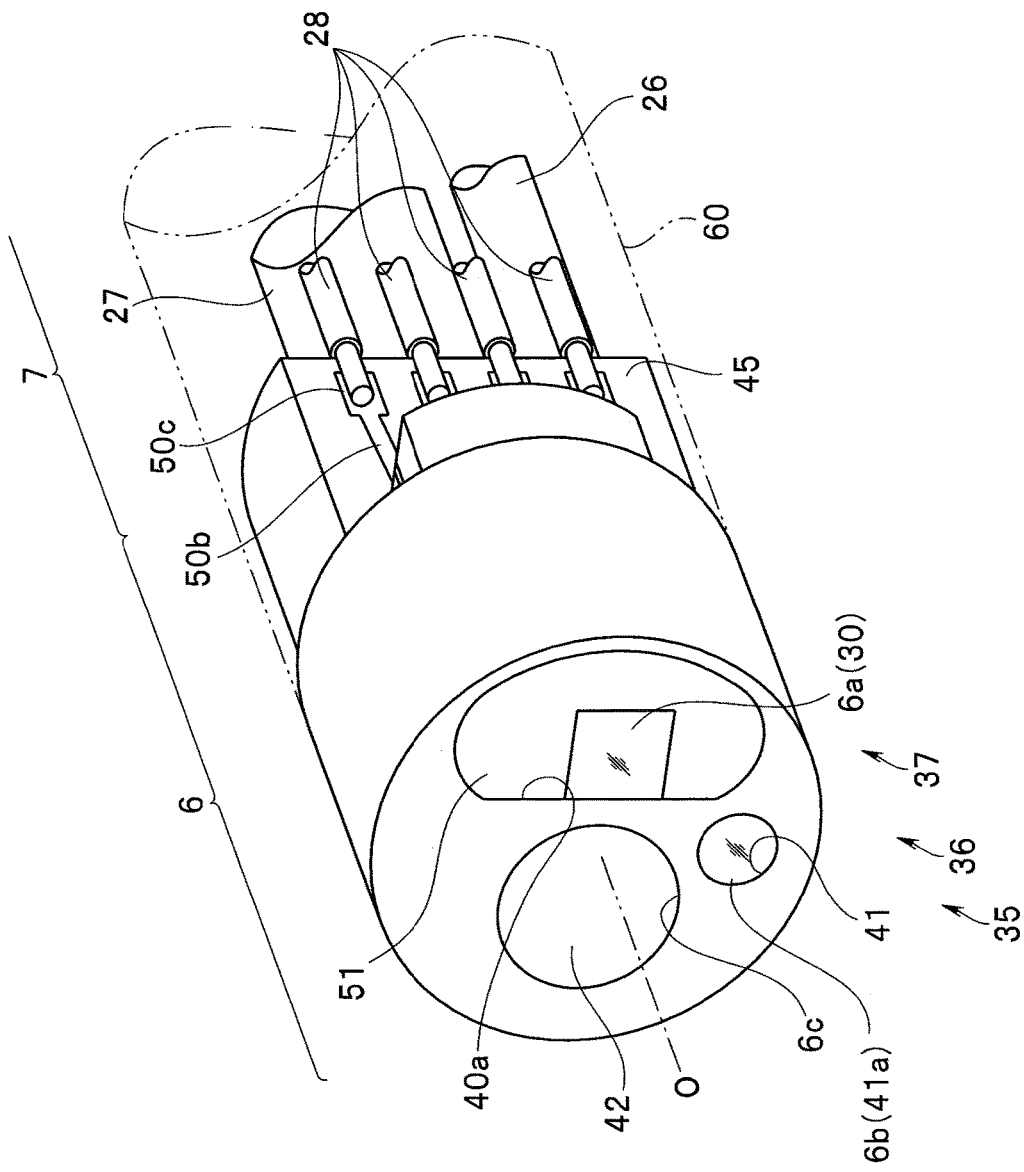
FIG. 8 is an external perspective view of a distal end unit according to a second embodiment of the present invention.
Figure 9:
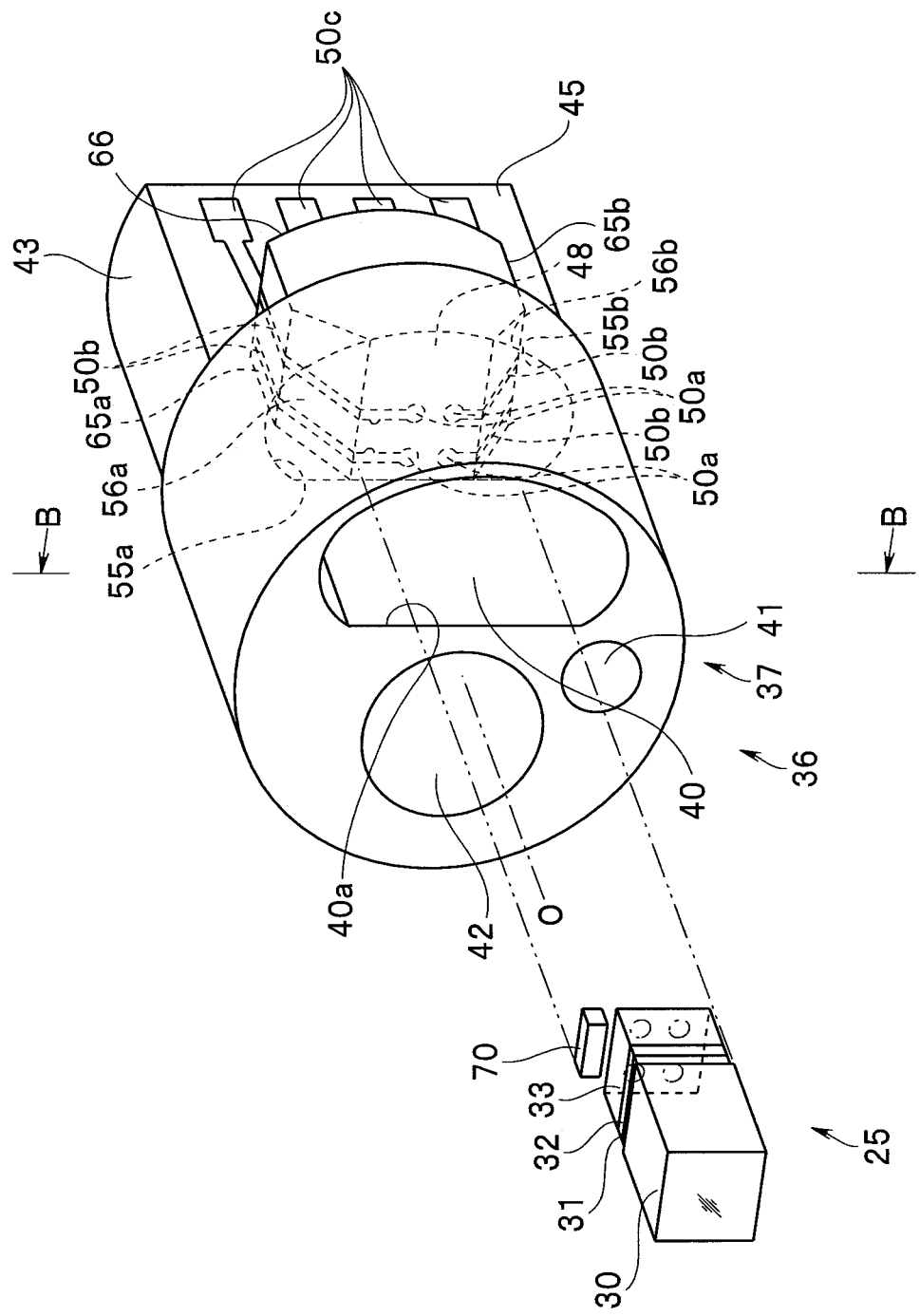
FIG. 9 is an exploded perspective view showing a distal end frame and an image pickup unit according to the second embodiment of the present invention.
Figure 10:
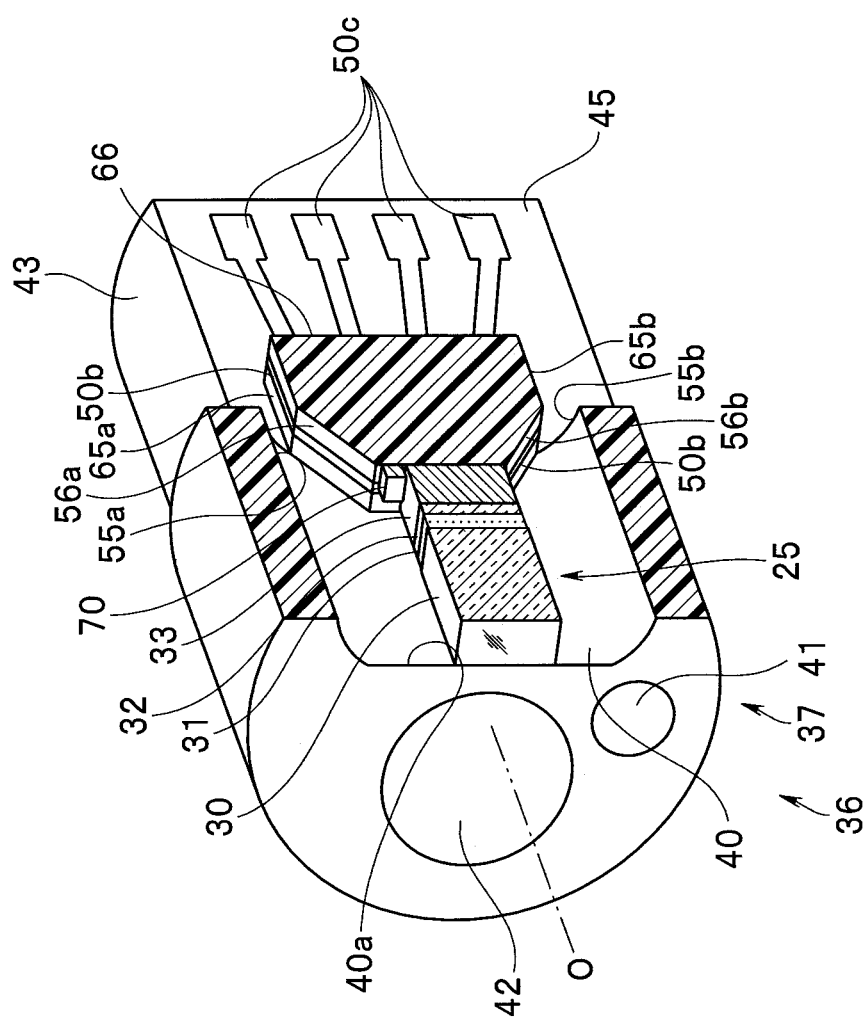
FIG. 10 is a cross-sectional view of a main part of the distal end frame along a line B-B in FIG. 9, according to the second embodiment of the present invention.
Figure 11:
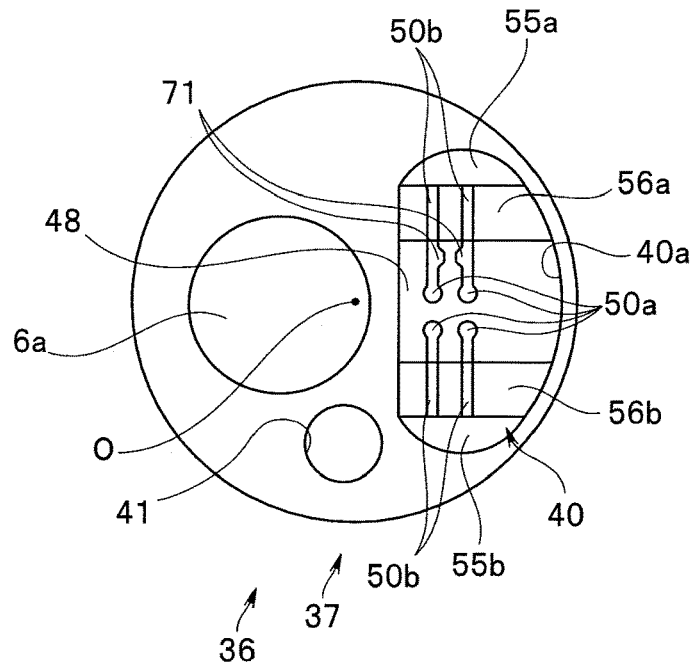
FIG. 11 is an end elevational view of the distal end frame according to the second embodiment of the present invention.
Figure 12:
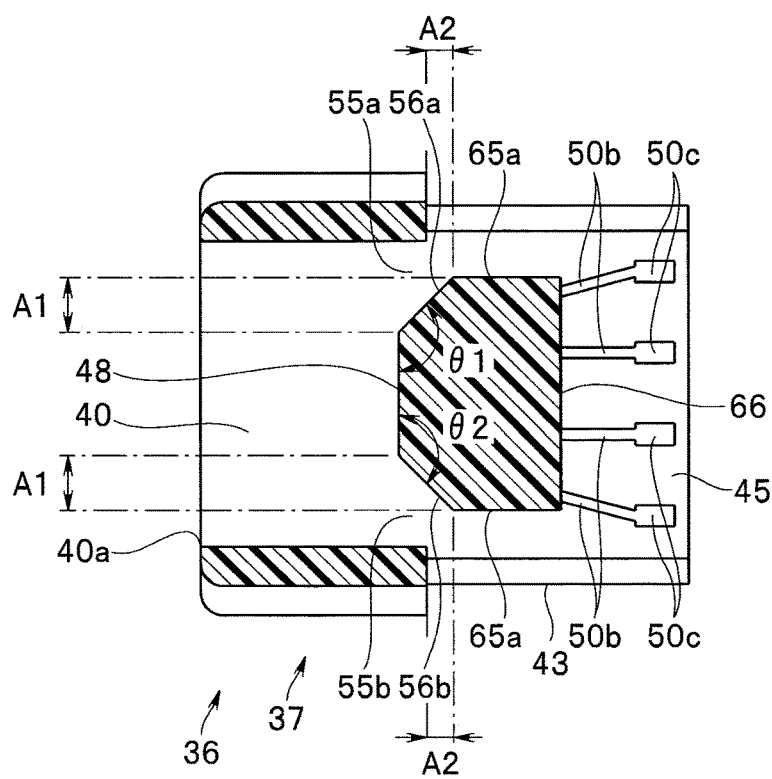
FIG. 12 is a cross-sectional view of the distal end frame along the line B-B in FIG. 9, according to the second embodiment of the present invention.

Next, FIG. 8 to FIG. 12 relate to a second embodiment of the present invention. FIG. 8 is an external perspective view of a distal end unit; FIG. 9 is an exploded perspective view of a distal end frame and an image pickup unit; FIG. 10 is a cross-sectional view of a main part of the distal end frame along a line B-B in FIG. 9; FIG. 11 is an end elevational view of the distal end frame; and FIG. 12 is a cross-sectional view of the distal end frame along the line B-B in FIG. 9.

Note that the first embodiment described above has a configuration in which the single through hole 55 (and inclined face 56) are continuously provided on one side of the mounting face 48, but on the other hand, the present embodiment differs mainly in that a first through hole 55a and a second through hole 55b as through holes (and first inclined face 56a and second inclined face 56b as inclined faces) are provided on one side and the other side of the mounting face 48, respectively. As for other components similar to the first embodiment described above, same signs will be appropriately added and the description will be omitted.

As shown in FIG. 12, in the present embodiment, a position of the mounting face 48 in the insertion axis O direction is set to be located closer to the distal end side than a position of a step configured to form a fitting portion 43 on the outer periphery of a distal end frame body 37.

As shown in FIG. 9 to FIG. 12, in the bottom face of the image pickup unit housing chamber 40 of the present embodiment, a first through hole 55a and a second through hole 55b which extend in the depth direction (that is, insertion axis O direction) of the image pickup unit housing chamber 40 are provided in a region adjacent to the mounting face 48. Due to the first and second through holes 55a and 55b, the internal space of the image pickup unit housing chamber 40 communicates with a region on the proximal end side of the distal end frame body 37 in which the cable connection face 45 is formed.

Here, when the first and second through holes 55a and 55b adjacent to the mounting face 48 are formed as above, the image pickup unit housing chamber 40 needs to be expanded by the corresponding space, but in the present embodiment, an expansion region for forming the first and second through holes 55a and 55b is set in a direction orthogonal to a straight line connecting the observation window 6a and the channel opening 6c, and thereby, the enlargement of the diameter of the distal end frame body 37 is suppressed. In other words, a space in such a direction becomes basically a dead space in many cases, and by effectively utilizing such a dead space, it becomes possible to secure a space for providing the first and second through holes 55a and 55b without increasing the diameter of the distal end frame body 37.

In the inner wall faces constituting the first through hole 55a and the second through hole 55b, a first inclined face 56a and a second inclined face 56b as the second face are formed in a part of the region which is provided continuously to the mounting face 48, respectively. The first and second inclined faces 56a and 56b are set at such an angle that angles θ1 and θ2 formed by the mounting face 48 are, for example, larger than 90 degrees and smaller than 180 degrees, respectively, as shown in FIG. 12. In other words, the first and second inclined faces 56a and 56b are inclined at a predetermined angle with respect to the insertion axis O direction, for example, to be displaced in the outer peripheral direction as the inclined faces head from the distal end side to the proximal end side of the distal end frame body 37. In other words, the inclined faces 56 are inclined with respect to the insertion axis O direction so that each opening area (opening area orthogonal to the insertion axis O direction) of the through holes 55 is gradually reduced from the distal end side to the proximal end side.

Thereby, for example, when the inside of the image pickup unit housing chamber 40 is viewed squarely from the opening 40a side as shown in FIGS. 11 and 12, the first and second inclined faces 56a and 56b and the mounting face 48 can be seen at the same time. In other words, the first and second inclined faces 56a and 56b of the present embodiment each have a first region A1 that is visible in the insertion axis O direction through the opening 40a.

Furthermore, the fitting portion 43 is formed into a partially cut-out shape, and thereby in each of the inner wall faces constituting the first and second through holes 55a and 55b, a part of a region is removed which includes a region facing each of the first and second inclined faces 56a and 56b. Thereby, the first and second inclined faces 56a and 56b are exposed to a side of the fitting portion 43 (distal end frame body 37). By thus being exposed, the first and second inclined faces 56a and 56b each have a second region A2 that is visible in a direction which intersects the insertion axis O direction (for example, orthogonal direction). Each of the second regions A2 in the first and second inclined faces 56a and 56b is set so that at least a part of each region overlaps with each first region A1, respectively.

Here, for example, as shown in FIG. 12, the cable connection face 45 of the present embodiment is extended in a direction orthogonal to the first and second inclined faces 56a and 56b. For the reason, the proximal ends of the first and second inclined faces 56a and 56b are connected continuously to the cable connection face 45, via a pair of first and second relay faces 65a and 65b each extending in the direction orthogonal to the mounting face 48, and a third relay face 66 provided continuously to proximal ends of the first and second relay faces 65a and 65b and parallel to the mounting face 48.

The wiring patterns 50b provided on the mounting face 48 are distributed and extended on the first and second inclined faces 56a and 56b, respectively, and the wiring patterns 50b are further extended on the cable connection face 45 via the first and second relay faces 65a and 65b and the third relay face 66, respectively.

In addition, other ends of the wiring patterns 50b extended on the cable connection face 45 are electrically connected to the second connection lands 50c, respectively.

According to such an embodiment, substantially the same action effect as the action effect in the first embodiment described above can be achieved.

In addition, in the present embodiment, the wiring patterns 50b can be distributed to the first and second inclined faces 56a and 56b, and accordingly, a width of each of the wiring patterns 50b and a space between each of the wiring patterns 50b can be set wide. Accordingly, it is possible to cope also with a signal of high frequency and high current. Furthermore, it is possible to optimize a relation between the width of each of the wiring patterns 50b and the space between each of the wiring patterns 50b (line and space of each of the wiring patterns 50b).

In addition, because the space between each of the wiring patterns 50b can be set wide, a third connection land 71 on which another electronic component such as a capacitor 70 is mounted can be provided on the mounting face 48.

Figure 13:
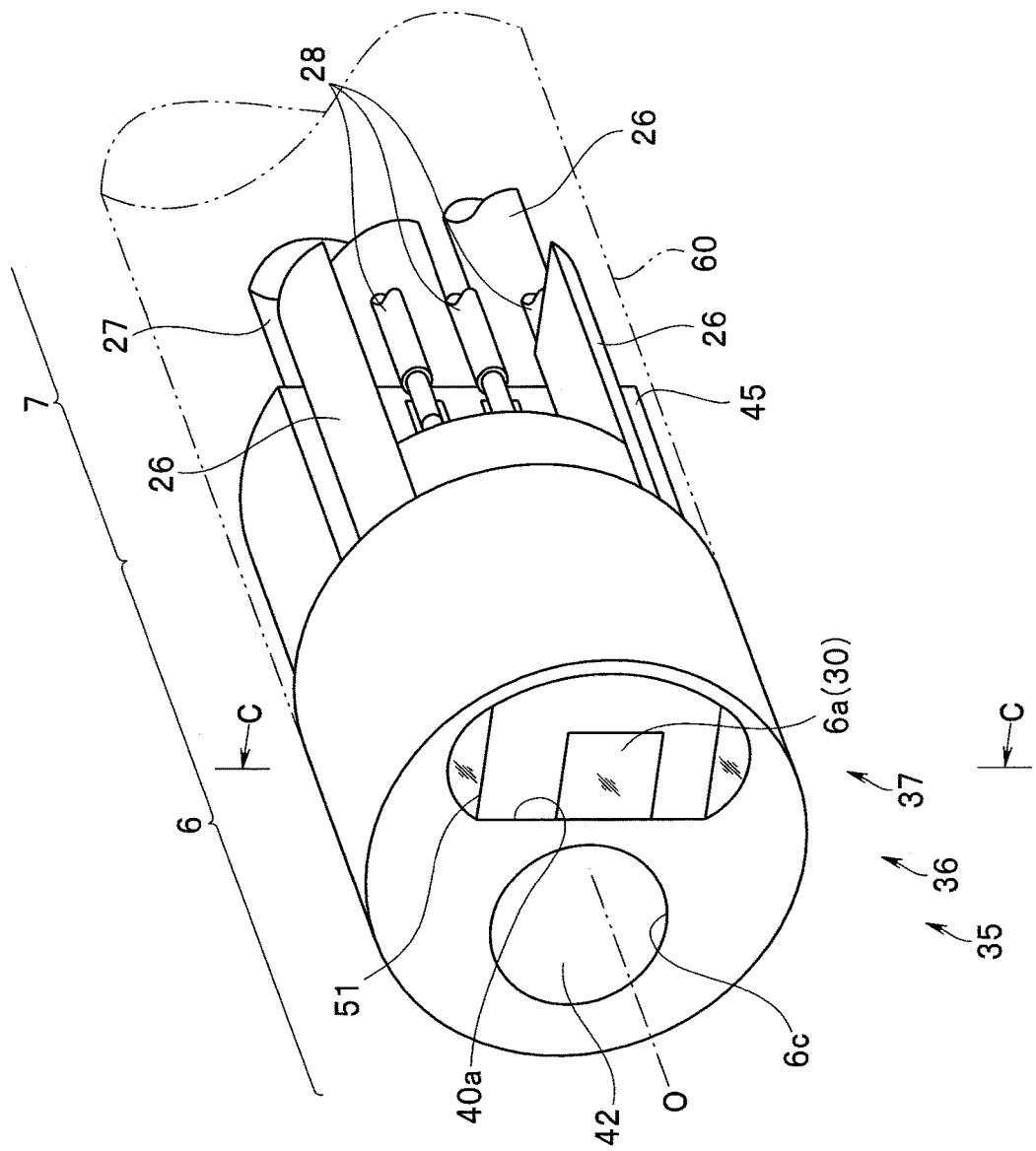
FIG. 13 is an external perspective view of a distal end unit according to a modification.
Figure 14:
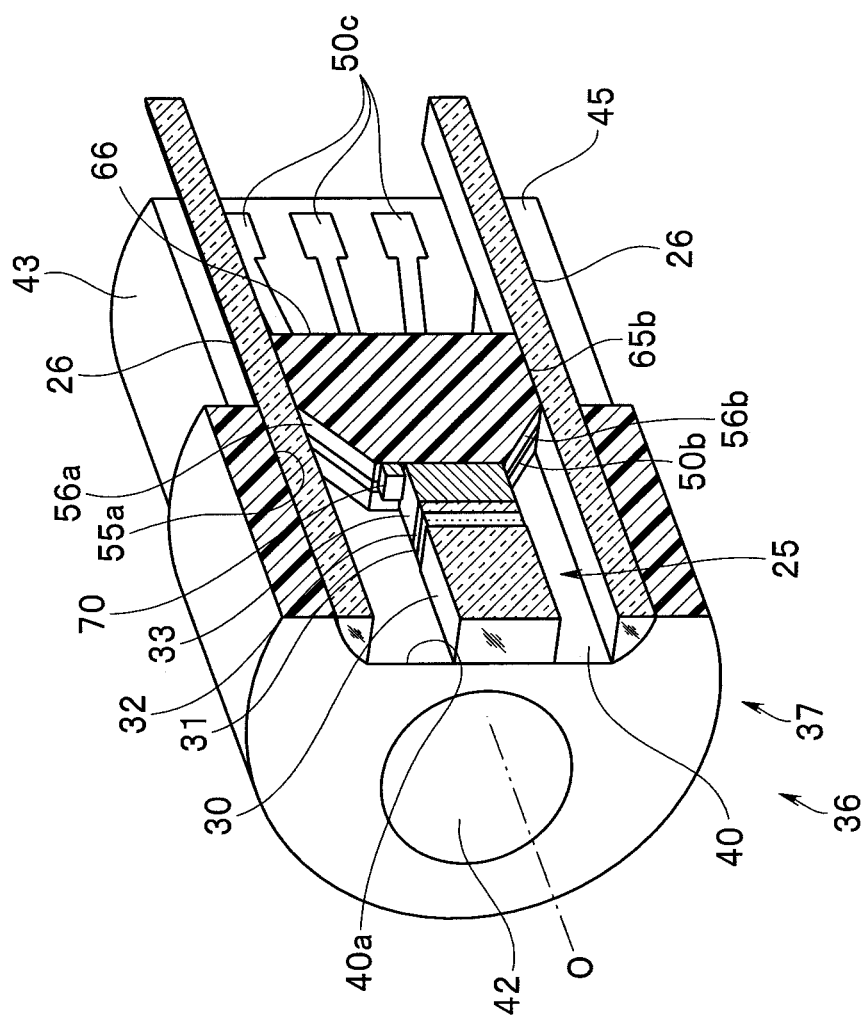
FIG. 14 is a cross-sectional perspective view showing a main part of the distal end unit along a line C-C in FIG. 13, according to the modification.

Here, for example, as shown in FIGS. 13 and 14, it is also possible to use the image pickup unit housing chamber 40 as the light source housing chamber, and use the first and second through holes 55a and 55b also as a through hole configured to allow insertion of the light guide 26.

The present invention is not limited to the respective embodiments described above, and various modifications and changes can be made, which are also within the technical scope of the present invention. For example, the application of the present invention is not limited to the image pickup unit housing chamber, and for example, in a case where a light emitting diode or the like is used as the light source instead of the light guide, a similar configuration can be adopted also for the light source housing chamber.

In addition, it goes without saying that the configurations of the respective embodiments and the respective modifications described above may be appropriately combined.

What is claimed is:

1. A distal end frame of an endoscope, comprising:
   a distal end frame body that comprises a resin molded product which constitutes a molded interconnect device having a metal pattern formed on a surface of the resin molded product;
   a housing chamber that is formed of a bottomed hole with an opening which is formed on an outer surface of the distal end frame body and is configured to open up an internal space, and that is configured to house an electronic component in an inside of the distal end frame body;
   a through hole that penetrates from a part of a bottom face of the housing chamber to a proximal end side of the distal end frame body;
   a first face that is formed on the bottom face of the housing chamber and on which the electronic component is mounted;
   a first connection land that is formed of the metal pattern constituting the molded interconnect device and is formed on the first face to electrically connect the electronic component;
   a second face that is formed in a region containing a part of an inner wall face of the through hole to be adjacent to the first face, and is visible through the opening; and
   a wiring pattern that is formed of the metal pattern constituting the molded interconnect device, is electrically connected to the first connection land, and is also continuously formed in a region containing the first face and the second face.

2. The distal end frame of the endoscope according to claim 1, further comprising: a third face that is formed in the distal end frame body to extend in a direction different from a direction of the second face at a side closer to a proximal end of the distal end frame body than the through hole; and a second connection land that is formed on the third face and is electrically connected to the wiring pattern.

3. The distal end frame of the endoscope according to claim 1, wherein
the second face comprises a first region that is visible in a depth direction of the housing chamber and a second region that is visible in a direction intersecting the depth direction of the housing chamber; and
the first region and the second region overlap at least partially.

4. The distal end frame of the endoscope according to claim 1, wherein
the through hole in plurality and the second face in plurality are formed for the housing chamber that is a single housing chamber.

5. A distal end unit of an endoscope, comprising:
a distal end frame including:
a distal end frame body that comprises a resin molded product which constitutes a molded interconnect device having a metal pattern formed on a surface of the resin molded product;
a housing chamber that is formed of a bottomed hole with an opening which is formed on an outer surface of the distal end frame body and is configured to open up an internal space, and that is configured to house the electronic component in an inside of the distal end frame body;
a through hole that penetrates from a part of a bottom face of the housing chamber to a proximal end side of the distal end frame body;
a first face that is formed on the bottom face of the housing chamber and on which the electronic component is mounted;
a first connection land that is formed of the metal pattern constituting the molded interconnect device and is formed on the first face to electrically connect the electronic component;
a second face that is formed in a region containing a part of an inner wall face of the through hole to be adjacent to the first face, and is visible through the opening; and
a wiring pattern that is formed of the metal pattern constituting the molded interconnect device, is electrically connected to the first connection land, and is also continuously formed in a region containing the first face and the second face; and
an electronic component that is housed in the housing chamber of the distal end frame and is electrically connected to the first connection land.

6. The distal end unit of the endoscope according to claim 5, wherein
the electronic component is an image pickup unit.

7. The distal end unit of the endoscope according to claim 5, wherein
in the distal end frame, the wiring pattern in plurality is formed in the through hole that is a single through hole.

8. An endoscope comprising in a distal end portion of an insertion portion:
a distal end frame including:
a distal end frame body that comprises a resin molded product which constitutes a molded interconnect device having a metal pattern formed on a surface of the resin molded product;
a housing chamber that is formed of a bottomed hole with an opening which is formed on an outer surface of the distal end frame body and is configured to open up an internal space, and that is configured to house the electronic component in an inside of the distal end frame body;
a through hole that penetrates from a part of a bottom face of the housing chamber to a proximal end side of the distal end frame body;
a first face that is formed on the bottom face of the housing chamber and on which the electronic component is mounted;
a first connection land that is formed of the metal pattern constituting the molded interconnect device and is formed on the first face to electrically connect the electronic component;
a second face that is formed in a region containing a part of an inner wall face of the through hole to be adjacent to the first face, and is visible through the opening; and
a wiring pattern that is formed of the metal pattern constituting the molded interconnect device, is electrically connected to the first connection land, and is also continuously formed in a region containing the first face and the second face; and
an electronic component that is housed in the housing chamber of the distal end frame and is electrically connected to the first connection land.

* * * * *